United States Patent [19]

Maas et al.

[11] Patent Number: 5,859,331

[45] Date of Patent: Jan. 12, 1999

[54] MODULAR PROMOTER CONSTRUCT

[75] Inventors: Christoph Maas; Jeff Schell, both of Cologne; Hans-Henning Steinbiss, Much, all of Germany

[73] Assignee: Maxplanck-Gesellschaft Zur Forderung Der Wissenschaften E.V., Gottingen, Germany

[21] Appl. No.: 362,454

[22] PCT Filed: Jul. 7, 1993

[86] PCT No.: PCT/EP93/01769

§ 371 Date: Feb. 7, 1995

§ 102(e) Date: Feb. 7, 1995

[87] PCT Pub. No.: WO94/01571

PCT Pub. Date: Jan. 20, 1994

[30] Foreign Application Priority Data

Jul. 8, 1992 [DE] Germany ............... 42 22 407.1

[51] Int. Cl.[6] ............ C12N 15/29; C12N 15/82; C12N 15/11; A01H 5/00

[52] U.S. Cl. ............ 800/205; 536/24.1; 536/23.6; 435/419; 435/320.1; 435/172.3

[58] Field of Search ............... 536/24.1, 23.6; 435/320.1, 240.4, 172.3, 419; 800/205

[56] References Cited

PUBLICATIONS

Zhang et al. The Plant Cell, vol. 3, pp. 1155–1165 (Nov. 1991) Analysis of Rice Act 1 5' Region Activity in Transgenic Rice Plants.

Maas et al. Plant Molecular Biology 16, pp. 199–207 (1991) The Combination of a Novel Stimulatory Element in the First Exon . . .

*Primary Examiner*—David T. Fox
*Assistant Examiner*—Thomas Haas
*Attorney, Agent, or Firm*—Oblon, Spivak, McClelland, Maier & Neustadt, P.C.

[57] ABSTRACT

A modular promoter construct is described which possesses a promoter which is active in plant cells and a DNA sequence from exon 1 of the rice actin 1 gene. This modular promoter construct gives rise, where appropriate together with additional regulatory DNA sequences, to a substantial increase in gene expression in plant cells.

8 Claims, 5 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

ACCACCACCA CCACCACCTC CTCCCCCTC GCTGCCGGAC GACGAGCTCC TCCC 54

MODULAR PROMOTER CONSTRUCT

BACKGROUND OF THE INVENTION

FIELD OF THE INVENTION

The invention relates to a modular promoter construct based on exon 1 of the actin 1 gene from rice.

There has always been the need to provide agronomically important cereal plants with improved properties. Previously, hereditary traits or genes were crossed into the plants concerned using classical methods. Since recombinant DNA technology has become established, it is possible to insert defined genes into the genome of cereal plants such as, for example, rice, maize, wheat and barley. In addition to selecting the correct selective marker gene and the agronomically important genes, the choice of the correct promoter is of crucial importance for effectively expressing the desired gene. The promoter which is used most for increasing the expression of chimeric genes in monocotyledonous cereal plants derives from the cauliflower mosaic virus (CaMV) 35S RNA gene (Odell et al., Nature 313, pages 810 to 820, 1985). However, as compared with its activity in dicotyledonous plants, this promoter is not very active in monocotyledonous plants (Töpfer et al., Meth. Enzymol., "Rec. DNA", in press). Thus, alternative gene expression vectors using strong promoters, such as the promoters of the actin 1 gene from rice (McElroy et al., Plant Cell 2, pages 163 to 171, 1990) and the ubiquitin gene from maize (Christensen and Fox, International Society for Plant Molecular Biology Meeting, Program Abstracts, No. 287, 1991).

In analogy with animal systems (Dynan, Cell 58, pages 1 to 4, 1989), it is probably also the case for plant genes as well that the transcription mediated by RNA polymerase II is dependent on modular elements, i.e. elements consisting of different regulatory DNA sequences. It has already been demonstrated that a number of different modular elements play an important role in, for example, tissue-specific transcription (Katagiri and Chua, Trends Gent. 8, pages 22 to 70, 1992).

Thus, DE-OS 41 24 537 discloses a modular promoter construction which can be used to increase the expression of foreign genes in plant cells. In this case, a DNA sequence from exon 1 of the sucrose synthase gene from Zea mays L. is inserted between the promoter and the gene to be expressed. A further, multiplicative increase in gene expression is possible if an additional DNA sequence, corresponding essentially to intron 1 of the sucrose synthase gene from Zea mays L., is coupled to the said DNA sequence.

McElroy et al., loc. cit., have described the isolation of promoter sequences of the rice actin 1 gene lying in the 5' region. It has emerged that there is a positive correlation between the promoter sequences and the subsequent intron sequences. Thus, in investigations of the transformation of rice protoplasts, a promoter construct of these sequences has proved to be an effective regulator of the constitutive expression of a foreign gene.

SUMMARY OF THE INVENTION

The underlying object of the present invention is to make available a promoter which can be used to express foreign genes in plants with a high degree of efficiency.

This object is achieved by a modular promoter construct according to Patent claim 1.

The subclaims relate to preferred embodiments of the novel promoter construct.

The invention thus relates to a modular promoter construct which has a promoter which is active in plant cells and a DNA sequence from exon 1 of the rice actin 1 gene, and to the alleles and derivatives of this modular promoter construct.

The invention furthermore relates to vectors which contain the novel promoter constructs.

The invention also relates to plant cells which are transformed with the said vectors.

The invention additionally relates to plants, and their descendants, which are regenerated from the said plant cells.

Finally, the invention also relates to the use of the novel promoter constructs for preparing plants having elevated gene expression.

DETAILED DESCRIPTION OF THE PREFERRED EMBODIMENTS

Figure 2:
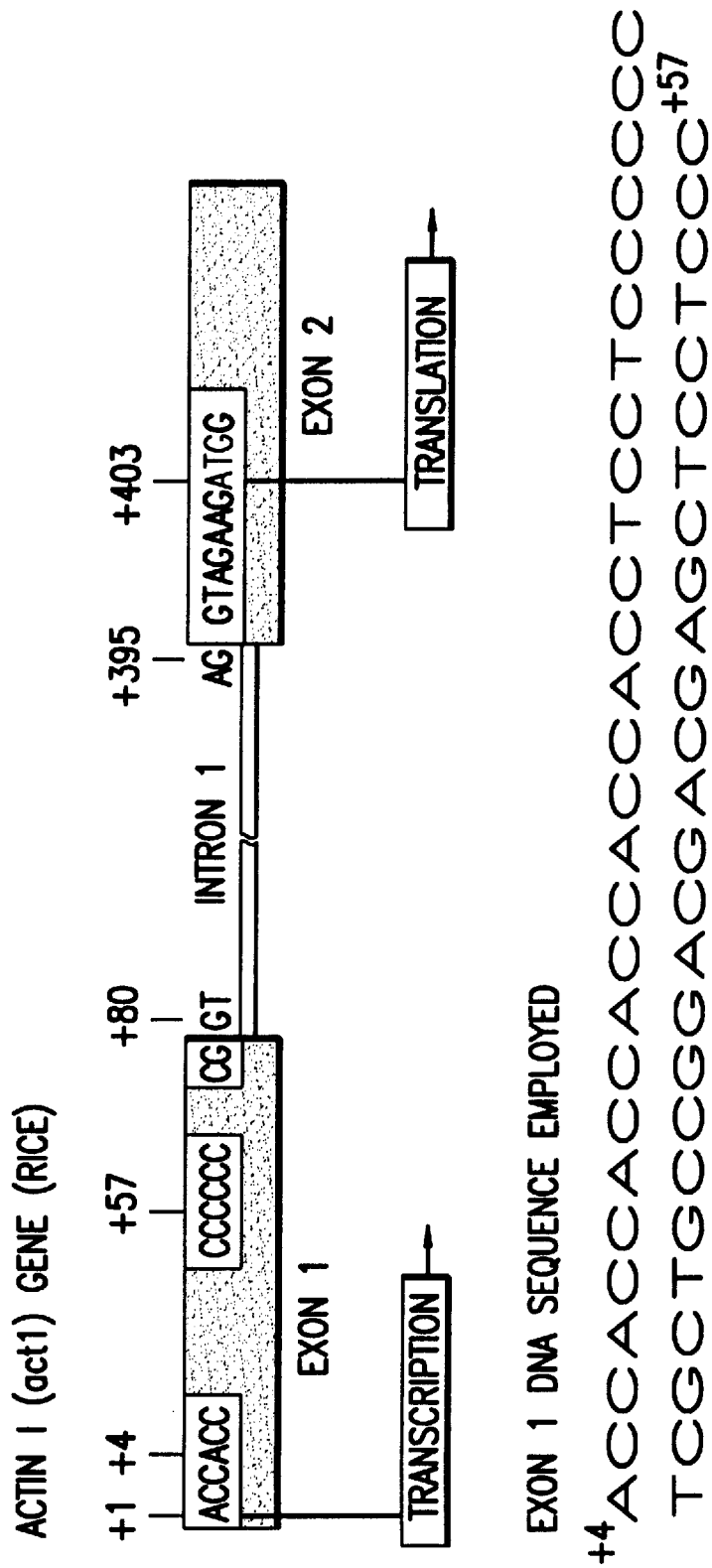
FIG. 2 shows a schematic representation of the rice actin 1 (act 1) gene with the exon 1 DNA sequence (SEQ ID NO:1) employed.

The novel promoter construct is a promoter which stimulates RNA polymerase II. The novel modular promoter construct possesses a promoter which is active in plant cells and a regulatory DNA sequence coupled to this promoter. This DNA sequence derives from exon 1 of the actin 1 gene (act1/exon1 sequence) from rice. The DNA sequence contained in the promoter construct preferably conforms to the sequence from positions +4 to +57 in exon 1 of the actin 1 gene, as shown in FIG. 2 (SEQ ID NO:1). The untranslated exon 1 is separated by an intron (intron 1) from the translation start point in exon 2. Exon 1 is thus situated in the 5' region of the actin 1 gene which is transcribed but not translated. The entire sequence of exon 1 of the said gene is given in McElroy et al., (loc. cit.).

The act1/exon1 sequence is GC-rich (77%) and acts as an RNA-polymerase II-stimulating element when it is located downstream of the transcription start site.

It has been found that when the novel modular promoter construct is coupled- to a gene which is to be expressed in a plant cell, the expression of this gene is then substantially increased, it being possible to observe at least a 10-fold increase in expression of the gene.

The expression of the gene can be elevated a further 100-fold if the act1/exon1 sequence is combined with intron 1 of the *Zea mays* sucrose synthase gene, surprisingly resulting in at least a 1000-fold increase in the expression of the gene.

It has emerged that the 18-bp OTF binding site of the octopine synthase promoter (OCS enhancer) is compatible for example, with the CaMV 35S promoter. If the OTF binding site is combined with the act1/exon1 sequence and intron 1 of the *Zea mays* L. sucrose synthase gene, the activity of the gene increases sharply by at least a factor of 4000.

It is evident from the above that gene expression can be multiplied depending on the regulatory DNA sequence which is coupled to the gene to be expressed. Thus, the novel modular promoter construct can be used to achieve a multiplication in gene activity.

The novel modular promoter constructs, and the vectors, contain, as a promoter which is active in plant cells, such as, for example, the CaMV 35S promoter, the nopaline synthase promoter or the sucrose synthase promoter.

The novel modular promoter construct is suitable for expressing all types of foreign genes, such as, for example, resistance genes, as disclosed, for example, in EP-A 0 257 542 and EP-A 0 275 957, and also for preparing proteinogenous active compounds in plants, for example in accordance with DD-A 12 65 164. Genes for storage proteins, such as, for example, zeins or hordeins, are of particular importance.

Downstream of the gene to be expressed, the novel modular promoter constructs, and the vectors which contain the novel promoter constructs, contain polyadenylation regions from the CaMV 35S gene or the octopine synthase (OCS) gene (Hein et al., Mol. Gen. Genet., 199, pages 161 to 168 (1985)).

The novel modular promoter construct is suitable for expressing foreign genes in monocotyledonous and dicotyledonous plants. Examples of suitable monocotyledonous plants are cereal plants, such as wheat, barley, maize and rice. Tobacco (*Nicotiana tabaccum*) is an example of a dicotyledonous plant which can be transformed satisfactorily.

It is self-evident that allelic variants and derivatives of the abovementioned modular promoter construct are also included within the scope of the invention, provided that these modified modular promoter constructs perform the same function as the above-mentioned promoter constructs, i.e. have a stimulatory effect on gene expression. The allelic variations and derivatives include, for example, deletions, substitutions, insertions, inversions or additions of the individual sequences of the novel promoter construct.

The transformation of plants with a foreign gene using the novel modular promoter construct can be carried out with the aid of customary transformation methods. That which is particularly preferred is protoplast transformation, followed by regeneration into a plant of the plant cells resulting from the transformed protoplasts.

Embodiments of the novel modular promoter construct which are particularly preferred are described in the following examples.

EXAMPLE 1

Plasmid Constructions

Figure 1:
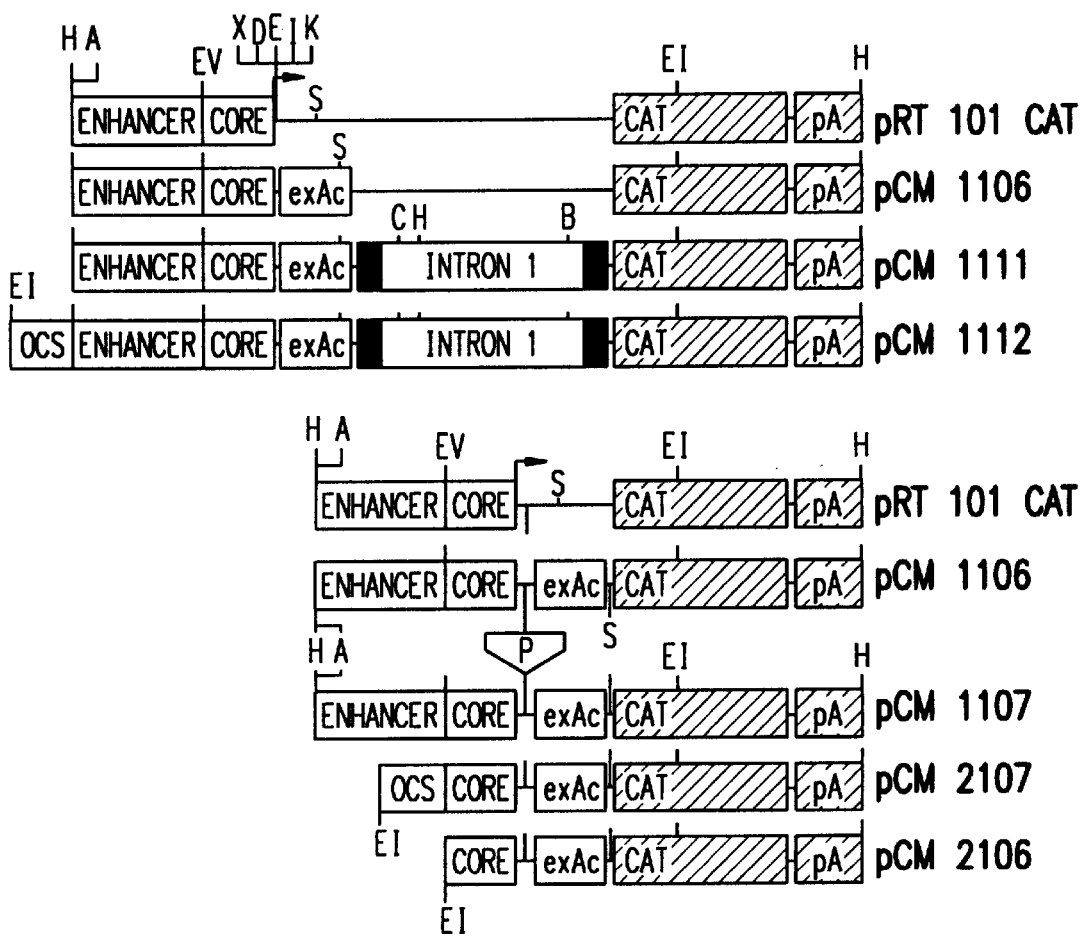
FIG. 1 shows chimeric gene constructs for transient gene expression experiments.

The plasmid constructions described below are given in FIG. 1. The chimeric gene constructions shown in this figure were used for transient gene expression experiments. The transcription start site and the CaMV 35S gene polyadenylation signal are the same in all constructions. The restriction sites which are of relevance to the cloning have also been included. The polylinker (P) between the transcription start and the translation start encompasses, from the 5' end to the 3' end, the restriction sites X, D, EI and K. The restriction sites are abbreviated as follows: BclI (B), EcoRI (EI), EcoRV (EV), HindIII (H), HincII (A), KpnI (K), SmaI (S), SstII (C) and XhoI (X). The CaMV 35S promoter is denoted by "enhancer core" and the OTF binding site by "OCS".

All the plasmid constructions were prepared by customary methods, as described, for example, in Sambrook et al., Molecular cloning: A laboratory manual, 2nd edition, Cold Spring Harbor Laboratory Press, Cold Spring Harbor, N.Y., 1989.

All the plasmid constructions are derived from the chimeric plasmid pRT 101 CAT ab (Pröls et al., Plant Cell. Rep. 7, pages 221 to 224, 1988), which contains the CAT marker gene (CAT=chloramphenicol transacetylase). In order to prepare the chimeric plasmid pCM 1106, the non-translated sequence of exon 1 of the actin 1 gene (act1/exon1 sequence) from positions +4 to +57 (SEQ ID No:1) was inserted into the unique SmaI restriction site (S) in the 5'-non-translated leader of the pRT 101 CAT plasmid. In this context, reference may be made to FIG. 2, which shows the sequence from exon 1 which is employed and its position within exon 1. Insertion of the said DNA sequence restores the SmaI restriction site due to 3'-terminal cytosine residues of the actin I element (see also FIG. 2, positions +55 to +57).

The intron I sequences from the maize sucrose synthase gene (Sh1) (positions +43 to +1084) are isolated as a HincII restriction fragment from the chimeric plasmid pSP 1076+ 1084, which is disclosed in DE-OS 41 24 537, and this fragment is inserted into the SmaI restriction site of pCM 1106. In this way, the chimeric plasmid construction pCM 1111 is obtained.

A DNA Synthesizer (Applied Biosystems 380 B) is used to synthesize the sequence from exon 1 of the rice actin 1 gene, shown in FIG. 2, and the 18-bp OTF binding site having the sequence AACGTAAGCGCTTACGTT (Ellis et al., EMBO J. 6, pages 3203 to 3208, 1987). The OTF binding site is then subcloned into the unique SmaI restriction site in the commercially available plasmid pUC 19, resulting in pOTF 18. In order to prepare the chimeric plasmids pCM 1112 and pCM 2107, a HincII (A)/HindIII (H) restriction fragment is isolated from pCM 1111 and pCM 2106 (HindIII is a partial digestion of pCM 1111) and inserted into the unique HincII restriction site in pOTF 18.

In order to prepare the plasmid pCM 1107, the polylinker in the chimeric plasmid pCM 1106 is removed by a restriction digestion using XhoI (X)/KpnI (K). The protruding ends are removed by careful treatment with S1. Autoligation results in the plasmid construct pCM 1107, which, in comparison to pCM 1106, has a deletion of 11 base pairs between the transcription start site and the act1/exon1 sequence.

The promoter deletion plasmid pCM 2106 is prepared by removing CaMV 35S promoter sequences from pCM 1106 upstream of the EcoRV (EV) restriction site at position -90.

EXAMPLE 2

2.1 Analysis of Transient Expression

Protoplasts are isolated from a cell suspension of the barley line *Hordeum vulgare* L. cv. Golden Promise in accordance with the method described for maize (Maas and Werr, Plant Cell. Rep. 8, pages 148 to 151, 1989), using an osmolarity of 720 mosm. A cell suspension of the line *Triticum monoccum* (one-grained wheat) was cultivated, and protoplasts were isolated, essentially as described by Lörz et al., Mol. Gen. Genet. 199, pages 178 to 182, 1985 and Matzeit et al., Plant Cell 3, pages 247 to 258, 1991).

The *Hordeum vulgare* and *Triticum monoccum* protoplasts were transformed as described in Maas and Werr loc. cit. and Maas et al., loc. cit. Approximately 1 x $10^6$ protoplasts are transformed with 25 µg of plasmid DNA and 100 µg of sonicated calf thymus DNA, and a PEG-mediated gene transfer is carried out (PEG solution: 25% PEG (1500), 0.1 M $MgCl_2$, pH 6.0). Gene expression is examined on the basis of the content of protein formed at from 15 to 19 hours after the transformation.

2.2 Determination of CAT Activity

For the determination of CAT activity, the transformed cells are centrifuged down, resuspended in 60 µl of 500 mM Tris/HCl at a pH of 7.5 (2 mM PMSF) and lysed by two cycles of freezing and thawing. The extract is clarified by centrifugation. 20 µl of the supernatant are used for determining protein in accordance with Bradford, Anal. Biochem. 72, pages 248 to 254, 1976. CAT activity is determined using thin-layer chromatography essentially as described by Gorman et al., Mol. Cell. Biol. 2, pages 1044 to 1051, 1982. The extracts were preincubated at 65° C. for 10 minutes, with 250 µg of BSA being added to the reaction mixture.

Two transformations were carried out in parallel for each plasmid construct. The treated protoplasts are cultured and combined in order to reduce the differences due to the different transformation efficiencies. One half (one×$10^6$ protoplasts) of this mixture is analysed for CAT activity. Owing to the high CAT activities in undiluted extracts, a series of 1:10 dilutions (1:10, 1:100, 1:1000) is prepared in order thereby to obtain linear CAT activities for the densitometric examination of the autoradiographs.

2.3 Investigation Results 2.3.1 *Hordeum vulgare*

The investigations of gene expression in *Hordeum vulgare* protoplasts containing the chimeric plasmids described in Example 1 led to the following results.

Figure 3:
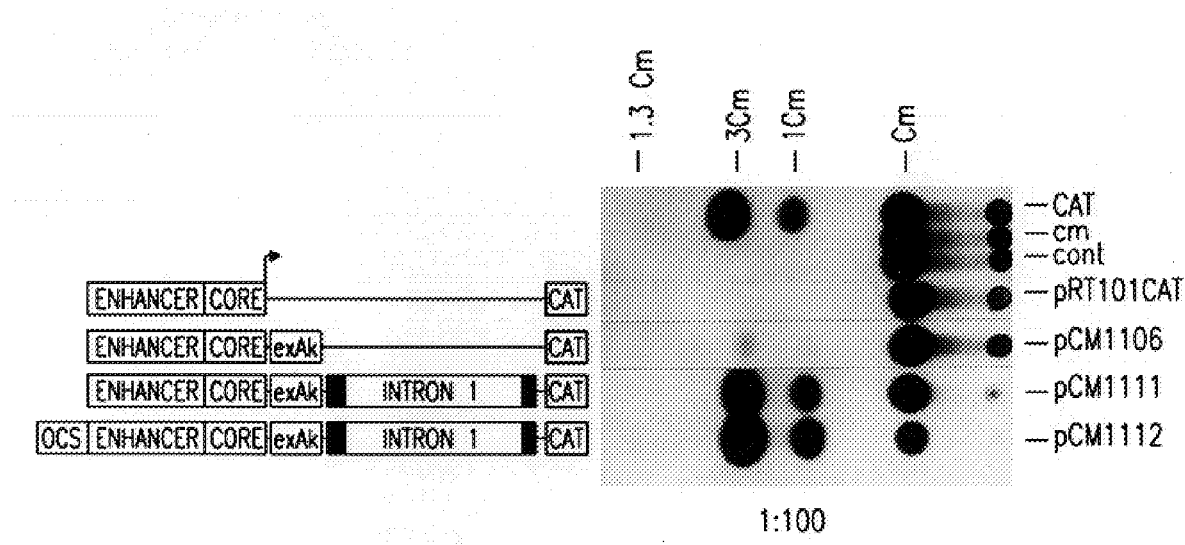
FIG. 3 shows a thin layer chromatogram of the transient expression of chimeric constructs in *Hordeum vulgare* protoplasts.

The results for the relative CAT activities can be seen from the thin-layer chromatogram in FIG. 3. Due to the high CAT activities in the crude extract, the activity was measured in a 1:100 dilution containing 1×$10^4$ protoplasts. The abbreviations have the following meanings: CAT= chloramphenicol transacetylase; Cm=$C^{14}$-labelled chloramphenicol alone; cont=protein extracts of non-transformed control protoplasts, and 1, 3, and 1, 3 Cm=chloramphenicol acetylated at the given positions.

There is at least a 10-fold increase in marker gene expression in the case of the chimeric plasmid pCM 1106 as compared with the reference plasmid pRT 101 CAT.

It can be seen from the chimeric plasmid pCM 1111 that marker gene expression is increased at least 1000-fold when the act1/exon1 sequence is combined with the intron 1 sequences from the sucrose synthase gene.

The 18-bp OTF binding site of the octopine synthase promoter, together with the entire CaMV 35S promoter, can interact with the act1/exon1 sequence and intron 1 of the sucrose synthase gene. Insertion of the OTF binding site into the chimeric plasmid pCM 1111, which contains the act1/ exon1 sequence and sequences from intron 1 of the sucrose synthase gene, results in at least a further 3- to 4-fold increase in the stimulation ratio (see pCM 1112). This result is also obtained using a 1:1000-fold dilution (not shown). Thus, it is demonstrated unequivocally that the stimulatory effect of combining different individual DNA sequences is multiplicative and not additive.

In this connection, reference is made to Table 1 below, which lists the CAT activities, from FIG. 3, of the chimeric plasmids pCM 1106, pCM 1111 and pCM 1112 in *Hordeum vulgare* protoplasts in relation to that of the reference plasmid pRT 101 CAT (activity=1).

TABLE 1

| pRT 101 CAT | pCM 1106 | pCM 1111 | pCM 1112 |
| --- | --- | --- | --- |
| 1 | 7.5–12.5 | 872–1242 | 3897–6965 |

2.3.2. *Triticum monoccum*

The investigations of gene expression in *Triticum monoccum* protoplasts containing the chimeric plasmids described in Example 1 led to the following results.

Figure 4:
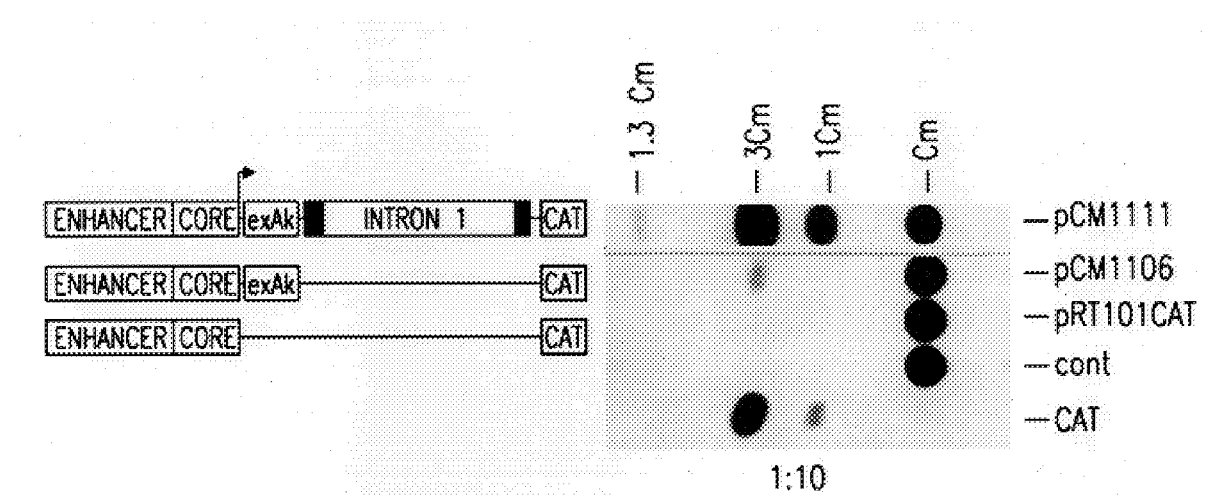
FIG. 4 shows a thin layer chromatogram of the transient expression of chimeric constructs in *Triticum monococcum* protoplasts.

As can be seen from FIG. 4, the same gene-expression stimulation ratios are obtained with transformed formed *Triticum monoccum* protoplasts as are obtained with *Hordeum vulgare* protoplasts. Thus, insertion of the act1/exon1 sequence results in at least a 10-fold increase in marker gene expression (pCM 1106). Combination of the act1/exon1 sequence with the intron 1 sequences of the sucrose synthase gene results in at least a 1000-fold increase in gene expression.

In this connection, reference may be made to Table 2 below, in which the CAT activities of the chimeric plasmids pCM 1106 and pCM 1111 from FIG. 4 are related to that of the chimeric reference plasmid pRT 101 CAT (activity=1).

TABLE 2

| pRT 101 CAT | pCM 1106 | pCM 1111 |
| --- | --- | --- |
| 1 | 7.5–11.9 | 913–1203 |

Figure 5:
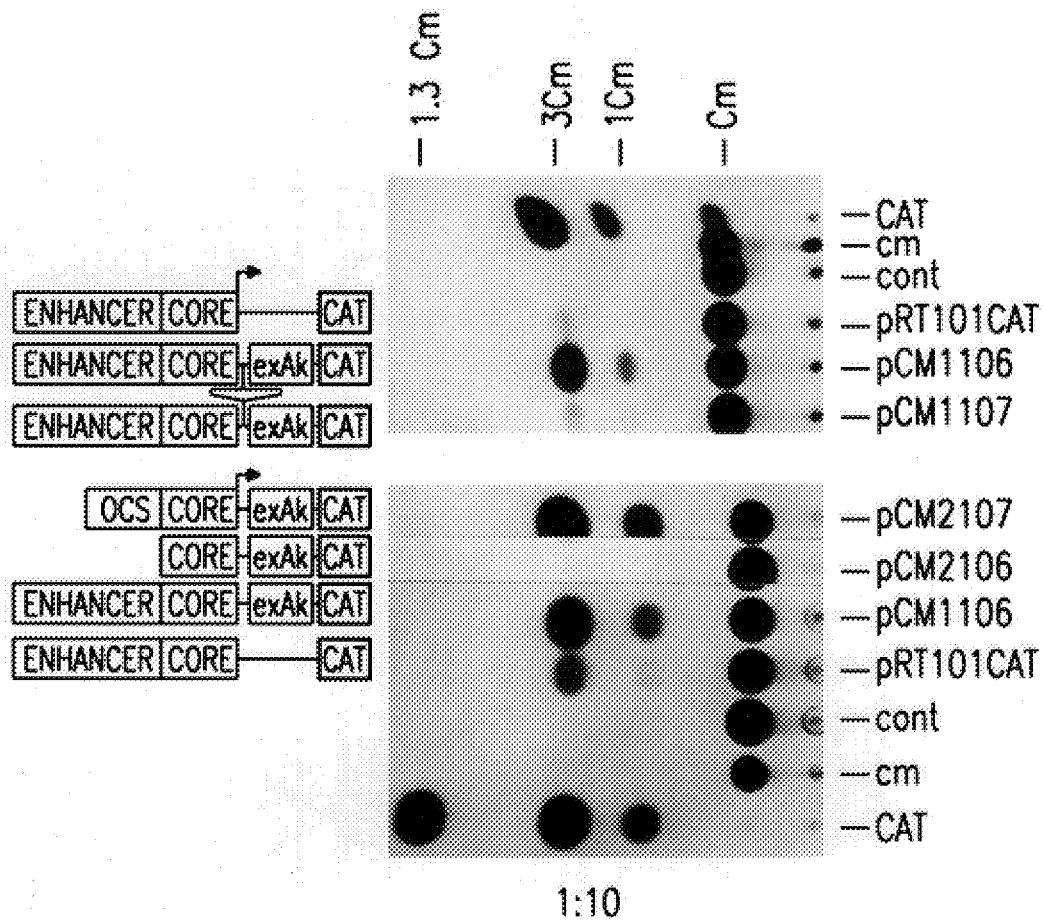
FIG. 5 shows a thin layer chromatogram of further transient gene expression in *Hordeum vulgare* protoplasts.

The thin-layer chromatogram in FIG. 5 demonstrates that the act1/exon1 sequence does not give rise to any increase in gene expression without the presence of upstream regulatory sequences. The act1/exon1 sequence increases marker gene expression at least 10-fold when it is inserted downstream of the entire CaMV 35S promoter (pCM 1106). By contrast, deletion of the CaMV 35S promoter in the chimeric plasmid pCM 1106 (pCM 2106, FIG. 1) completely abolishes the stimulatory ability of the act1/exon1 sequence.

Since, for effective marker gene expression, the act1/ exon1 sequence requires the presence of upstream regulatory elements, the activity of the chimeric plasmid pCM 2106 can be restored by inserting upstream regulatory elements. For this reason, the 18-bp OTF binding site was inserted, as a regulatory sequence, upstream of the CaMV 35S promoter of the chimeric plasmid pCM 2106 to form the chimeric plasmid pCM 2107 (see also FIG. 1). The transient gene expression of chimeric plasmid pCM 2107 shows that the act1/exon1 sequence in the non-stimulatory chimeric plasmid pCM 2106 once again displays its effect of stimulating by at least a factor of 10 if the plasmid contains the OTF binding site.

It can be seen from the examples of chimeric plasmids pCM 1106 and pCM 1107 that the distance to the transcription start site of the heterologous promoter is also very important. Deleting 11 base pairs in the polylinker of pCM 1106 which are located between the transcription start site and the act1/exon1 sequences abolishes the stimulatory effect of the promoter construct (pCM 1107). Accordingly, the distance between the transcription start site and the act1/exon1 sequence should preferably be at least 11 bp.

The relative values of the increases in gene expression, obtained with the chimeric plasmids shown in FIG. 5, are given in Table 3 below. In this table, the CAT activities of chimeric plasmids pCM 1106, pCM 1107, pCM 2106 and pCM 2107 in *Hordeum vulgare* protoplasts are related to that of the chimeric reference plasmid pRT 101 CAT (activity=1).

TABLE 3

| pRT 101 CAT | pCM 1106 | pCM 1107 | pCM 2106 | pCM 2107 |
|---|---|---|---|---|
| 1 | 8.1–12.4 | 0.8–1.2 | 0.8–1.15 | 8.9–14.5 |

The novel modular promoter construct is thus an effective promoter which is constructed from optionally selected individual regulatory DNA sequences, using which promoter it is possible to increase the expression of foreign genes in plant cells by a factor of up to at least 4000. A DNA sequence from the 5'-non-translated region of exon 1 of the rice actin 1 gene is of central importance. This sequence is a cis element which stimulates RNA polymerase II, which must be located downstream of the transcription start site and which only displays its stimulatory effect on gene expression in the presence of upstream regulatory DNA sequences.

2. The modular promoter construct according to claim 1, wherein said DNA sequence has the sequence of SEQ ID NO: 1.

3. The modular promoter construct according to claim 1, further comprising a DNA sequence from intron 1 of the maize sucrose synthase gene.

4. The modular promoter construct according to claim 3, further comprising an 18-bp OTF binding site.

5. A vector comprising a promoter construct which comprises a promoter which is active in plant cells and a DNA sequence of at least 30 bases from exon 1 of the rice actin 1 gene, or derivatives of this modular promoter construct which have promoter activity, wherein said promoter construct is coupled to a gene which is expressed in a plant cell, and wherein said promoter is not a rice actin 1 gene promoter.

6. A plant cell which is transformed with a vector comprising a promoter construct which comprises a promoter which is active in plant cells and a DNA sequence of at least 30 bases from exon 1 of the rice actin 1 gene, or derivatives of this modular promoter construct which have promoter activity, wherein said promoter construct is coupled to a gene which is to be expressed in a plant cell, and wherein said promoter is not a rice actin 1 gene promoter.

7. A plant or its descendants, regenerated from a plant cell comprising a promoter construct which comprises a promoter which is active in plant cells and a DNA sequence of at least 30 bases from exon 1 of the rice actin 1 gene, or derivatives of this modular promoter construct which have promoter activity, wherein said promoter construct is coupled to a gene which is to be expressed in a plant cell, and wherein said promoter is not a rice actin 1 gene promoter.

8. A method for preparing plants having elevated gene expression, said method comprising transforming a plant cell with a vector comprising a promoter construct which comprises a promoter which is active in plant cells and a DNA sequence of at least 30 bases from exon 1 of the rice

We claim:

1. A modular promoter construct, comprising a promoter which is active in plant cells and a DNA sequence of at least 30 bases from exon 1 of the rice actin 1 gene, or derivatives of this modular promoter construct which have promoter activity, wherein said promoter is not a rice actin 1 gene promoter.

actin 1 gene, or derivatives of this modular promoter construct which have promoter activity, wherein said promoter construct is coupled to a gene which is to be expressed in a plant cell, and wherein said promoter is not a rice actin 1 gene promoter.

\* \* \* \* \*